United States Patent
Zhao et al.

(10) Patent No.: US 8,538,553 B2
(45) Date of Patent: Sep. 17, 2013

(54) MRI COMPATIBLE IMPLANTABLE LEAD

(75) Inventors: Yong D. Zhao, Simi Valley, CA (US); Rolf Hill, Jarfalla (SE); Ingmar Viohl, Milwaukee, WI (US); Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 310 days.

(21) Appl. No.: 12/889,189

(22) Filed: Sep. 23, 2010

(65) Prior Publication Data

US 2011/0079423 A1    Apr. 7, 2011

Related U.S. Application Data

(60) Provisional application No. 61/249,184, filed on Oct. 6, 2009.

(51) Int. Cl.
*A61N 1/00* (2006.01)

(52) U.S. Cl.
USPC .......................................................... 607/116

(58) Field of Classification Search
USPC .......................................................... 607/116
See application file for complete search history.

(56) References Cited

U.S. PATENT DOCUMENTS

| | | | |
|---|---|---|---|
| 7,015,393 B2 | 3/2006 | Weiner et al. | |
| 7,123,013 B2 | 10/2006 | Gray | |
| 7,174,219 B2 | 2/2007 | Wahlstrand et al. | |
| 2005/0070972 A1 | 3/2005 | Wahlstrand et al. | |
| 2005/0222647 A1 | 10/2005 | Wahlstrand et al. | |
| 2005/0222658 A1* | 10/2005 | Hoegh et al. | 607/116 |
| 2006/0200218 A1 | 9/2006 | Wahlstrand | |
| 2006/0247747 A1 | 11/2006 | Olsen et al. | |
| 2006/0247748 A1 | 11/2006 | Wahlstrand et al. | |
| 2007/0106332 A1 | 5/2007 | Denker et al. | |
| 2007/0112398 A1 | 5/2007 | Stevenson et al. | |
| 2007/0168006 A1 | 7/2007 | Gray | |

(Continued)

FOREIGN PATENT DOCUMENTS

| | | |
|---|---|---|
| EP | 2025361 A1 | 11/2007 |
| EP | 1883449 B1 | 1/2009 |
| WO | 2005102445 A1 | 11/2005 |
| WO | 2005102446 A1 | 11/2005 |

*Primary Examiner* — Christopher D Koharski
*Assistant Examiner* — Philip Edwards

(57) ABSTRACT

An implantable lead is provided that includes a lead body configured to be implanted in a patient. The lead body has a distal end and a proximal end, and a lumen extending between the distal and proximal ends and includes a connector assembly provided at the proximal end of the lead body. The connector assembly is configured to connect to an implantable medical device and includes an electrode provided proximate to the distal end of the lead body with the electrode configured to at least one of deliver stimulating pulses and sense electrical activity. A multi-layer coil is located within the lumen and extends at least partially along a length of the lead body. The coil includes a first winding formed with multiple winding turns, the winding turns being segmented in an alternating pattern of insulated segments and non-insulated segments along the length of the lead body. The multi-layer coil further includes a winding turn connective layer extending along and interconnecting the winding turns within at least one of the non-insulated segments. The multi-layer coil further includes a first winding formed with multiple winding turns, the winding turns being segmented into an alternating pattern of insulated segments and non-insulated segments along a length of the winding with a winding turn connective layer extending along and interconnecting the winding turns within at least one of the non-insulated segments.

20 Claims, 11 Drawing Sheets

(56) References Cited

U.S. PATENT DOCUMENTS

| | | |
|---|---|---|
| 2007/0299490 A1 | 12/2007 | Yang et al. |
| 2008/0033497 A1 | 2/2008 | Bulkes et al. |
| 2008/0049376 A1 | 2/2008 | Stevenson et al. |
| 2008/0116997 A1* | 5/2008 | Dabney et al. ............ 333/182 |
| 2008/0132986 A1 | 6/2008 | Gray et al. |
| 2008/0161886 A1 | 7/2008 | Stevenson et al. |
| 2009/0099440 A1 | 4/2009 | Viohl |
| 2009/0099555 A1 | 4/2009 | Viohl et al. |

* cited by examiner

MRI COMPATIBLE IMPLANTABLE LEAD

CROSS REFERENCE TO RELATED APPLICATIONS

This application claims the benefit of U.S. Provisional Application Ser. No. 61/249,184, filed Oct. 6, 2009.

FIELD OF THE INVENTION

Embodiments of the present invention generally relate to MRI compatible leads, and more particularly to MRI compatible leads that utilize a zebra coil configuration.

BACKGROUND OF THE INVENTION

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like (hereafter generally "implantable medical devices" or "IMDs". IMDs commonly employ one or more conductive leads that either receive or deliver voltage, current or other electromagnetic pulses from or to an organ or its surrounding tissue for diagnostic or therapeutic purposes. The leads include bare or insulated coiled wire forming one or more tightly wound solenoid-like structures along the shafts. These tightly wound coils facilitate torque transfer, prevent "buckling" and allow the conduction of electrical signals to and from the proximal (system) end to the distal (patient) end of the device. The lead may represent a catheter, an ICD lead, a neurostimulation lead, a pacemaker lead and the like. When exposed to electromagnetic fields, such as for example those present in magnetic resonance imaging ("MRI") systems, these leads may sustain undesired currents and or voltages that interact with the surrounding blood and tissue, potentially resulting in unwanted tissue heating, nerve stimulation or other negative effects resulting in erroneous diagnosis or therapy delivery.

The catheter-type lead may incorporate conductive surfaces for the transfer of diagnostic and therapeutic electromagnetic signals as well as mechanical torque transfer. The catheter-type lead includes a distal tip electrode, which is commonly used to deliver energy to the target tissue and to receive electrical signals from the tissue it contacts. The catheter-type lead also includes proximal electrodes, which are typically used to receive electrical signals from the tissue they are contacting. This type of catheter structure is encountered in cardiac ablation and EP mapping catheters, for example. The electrical contact between the proximal end of the catheter and the electrodes is typically made via a bundle of individually insulated wires or conductors. An outer coil structure is typically used for torque transfer and is not in contact with the electrodes. The outer coil and the wires sometimes sustain currents when exposed to an electromagnetic field, such as for example that encountered in an MRI system. These currents may induce heating or cause nerve stimulation in the tissue surrounding the device either directly or by creating current pathways through the tissue that interacts with the electrodes.

Another example of a lead is a pacemaker or ICD lead which incorporates conductive wires for the transfer of diagnostic and therapeutic electromagnetic signals, as well as mechanical torque transfer. The lead includes a distal tip electrode, which is commonly used to deliver energy to the target tissue and to receive electrical signals from the tissue it contacts. The lead also includes a proximal electrode, which is mostly used to receive electrical signals from the tissue in its vicinity. In pacemaker and ICD leads, the conductive paths or coiled wires are connected to the electrodes, and are typically surrounded by dielectric materials. The conductive paths provided by coiled wires can sustain unwanted currents when exposed to an electromagnetic field, such as for example encountered in an MRI system. These currents can induce heating in the tissue surrounding the device either directly or by creating current pathways through the tissue involving the electrodes and the pathways.

One approach to form the braiding of a lead is to wind a bare, thin wire on a flexible former. In some constructions, a thin insulated wire is used instead of the bare wire in an attempt to form an inductor extending along the full length of the lead. The inductor acts as a "choke" to suppress currents from propagating along the body of the lead. Because of the small pitch utilized, the formed coil, even with wire insulated, may not be entirely electrically equivalent to a pure inductor over the full frequency spectrum of interest.

More recently, an alternative coil structure has been proposed that is referred to as a "zebra" coil. The zebra coil structure includes a series of insulated coil segments that are separated by non-insulated, bare coil segments. The bare segments of the coil conductor interconnect the insulated coil segments. The series of insulated coil segments form a series of self resonant RF chokes in the lead body and operates to reduce MRI RF heating. The RF chokes represent low pass filters, as in discrete inductors, and are generated by the inductance and capacitance in the insulated coil segments.

However, opportunities still remain to improve upon the performance of the existing zebra coil structure. In the existing zebra coil, it is preferable that the insulated segments are long enough to minimize the electromagnetic interactions or couplings between the insulated coil segments. However, as the bare coil segments increase in length the potential increases that the bare coil segments may introduce unfavorable high DC resistance in the lead body.

Also, it is preferable that the zebra coil exhibit stable self resonance such that the resonant frequency of each RF choke does not vary substantially. The resonance frequency of the RF chokes, created by the insulated coil segments, is impacted by the DC resistance of the non-insulated, bare coil segments. Thus, as the DC resistance of the bare coil segments varies up/down, the resonant frequency of the RF chokes varies.

During operation, once a lead is implanted, the lead body will be deformed cyclically, such as with heart beats. This means that adjacent turns in the bare coil segments may cyclically move between states in which adjacent turns transition between a state where they electrically engage with one another and electrically disengage from one another. Also, certain types of leads include a single filar or wire in each coil, while other types of leads include multiple filars in each coil. Hence, the potential exists that adjacent filars in a multi-filar coil will also move between engaged and disengaged states throughout the deformation cycle. The changes in conductive connections between adjacent filars and adjacent turns in the coil, present an unstable mechanical connection which causes the conductive pathway to continuously, cyclically vary. Hence, the DC resistance also varies continuously and cyclically in the bare segments which will impact the resonant frequency of the RF chokes created by the insulated coil segments.

A need remains for an improved MRI compatible lead that addresses the above problems and other issues that will be apparent from the following discussion and figures.

SUMMARY

In accordance with one embodiment, an implantable lead is provided. The implantable lead includes a lead body configured to be implanted in a patient. The lead body has a distal end and a proximal end, and a lumen extending between the distal and proximal ends and includes a connector assembly provided at the proximal end of the lead body. The connector assembly is configured to connect to an implantable medical device and includes an electrode provided proximate to the distal end of the lead body with the electrode configured to at least one of deliver stimulating pulses and sense electrical activity. A multi-layer coil is located within the lumen and extends at least partially along a length of the lead body. The coil includes a first winding formed with multiple winding turns, the winding turns being segmented in an alternating pattern of insulated segments and non-insulated segments along the length of the lead body. The multi-layer coil further includes a winding turn connective layer extending along and interconnecting the winding turns within at least one of the non-insulated segments.

In another embodiment, a multi-layer coil for use in an implantable lead is provided. The multi-layer coil includes a first winding formed with multiple winding turns, the winding turns being segmented into an alternating pattern of insulated segments and non-insulated segments along a length of the winding with a winding turn connective layer extending along and interconnecting the winding turns within at least one of the non-insulated segments.

At least certain embodiments of the present invention add one or more electrical circuit pathways to interconnect the turns or filars in the bare coil or cable segments. The additional circuit pathways facilitate maintenance of stable and small DC resistance during the cyclical deforming in the lead. At least certain embodiments utilize various combinations of inner and outer bare coil segments, as well as inner and outer insulated coil segments.

DETAILED DESCRIPTION

Figure 1:
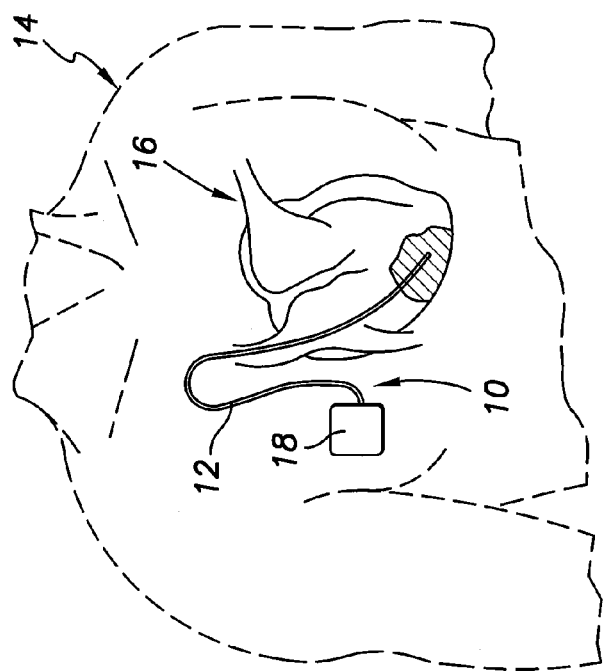
FIG. 1 illustrates an implantable medical system including an implantable lead formed in accordance with an exemplary embodiment.

FIG. 1 illustrates an implantable medical system 10 including an implantable lead 12 formed in accordance with an exemplary embodiment. FIG. 1 depicts a chest cavity 14 in phantom, and a heart 16 within the chest cavity 14. The medical system 10 includes an implantable medical device (IMD) 18 and the lead 12, which are both implanted in the chest cavity 14. Optionally, the medical device 18 may be implanted elsewhere, such as in the patient's abdomen, neck, pelvis regions, etc. In the illustrated embodiment, the lead 12 is a pacing and sensing lead. However, other types of leads may be used in alternative embodiments, such as neuromodulation leads, defibrillation leads, patient monitoring leads and the like. Although the following embodiments are described principally in the context of pacemaker/defibrillator unit capable of sensing and/or pacing pulse delivery, the medical system 10 may be applied to other IMD structures. As further examples, embodiments may be implemented in leads for devices that suppress an individual's appetite, stimulate the patients nervous or muscular systems, stimulate the patient's brain functions, reduce or offset pain associated with chronic conditions and control motor skills for handicap individuals, and the like.

Figure 2:
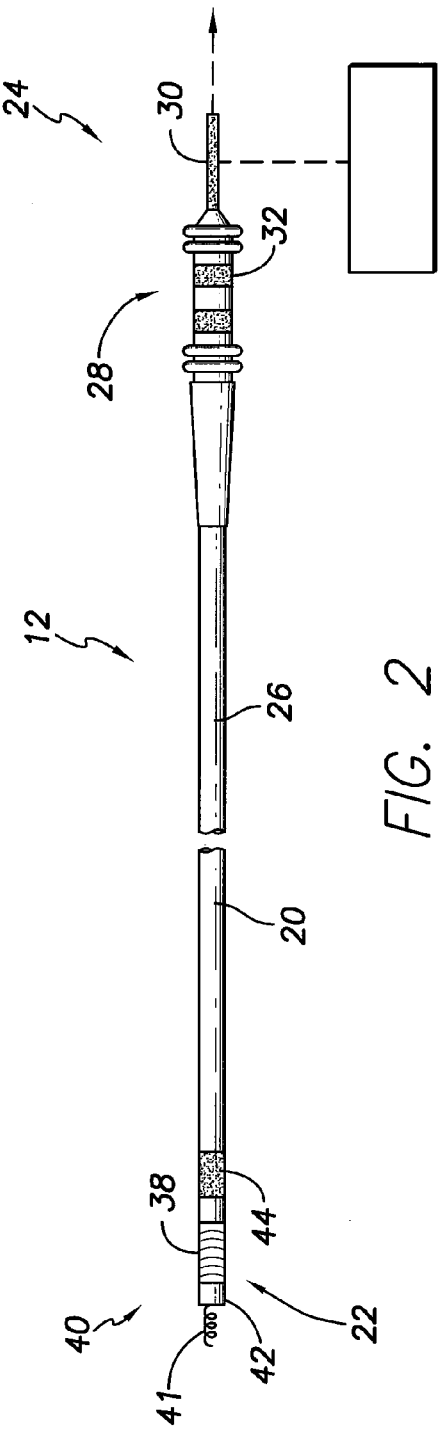
FIG. 2 illustrates the lead as having an elongated lead body which includes a distal end portion and a proximal end portion formed in accordance with an exemplary embodiment.

FIG. 2 illustrates the lead 12 as having an elongated lead body 20 which includes a distal end portion 22 and a proximal end portion 24. The lead body 20 has a length that extends along a longitudinal axis between the distal and proximal end portions 22 and 24. The term longitudinal axis encompasses both linear and non-linear axes. The longitudinal axis of the lead body 20 extends along a curved path that changes as the lead body 20 is flexed, bent and otherwise manipulated. The lead body 20 includes an insulating sheath 26 of a suitable insulative, biocompatible, biostable material such as, for example, PEEK (i.e. Polyetheretherketones), silicone rubber or polyurethane, extending substantially the entire length of the lead body 20.

Connector assembly 28 is provided at the proximal end portion 24 of the lead 12. The connector assembly 28 is configured to be inserted into a receiving orifice in the IMD 18. The connector assembly 28 includes first and second electrical terminals 30, 32 each being connected to respective electrical conductors, such as pacing and sensing electrical conductors, within the lead 12.

Header assembly 40 is provided at the distal end portion 22 of the lead 12. The header assembly 40 includes a tip electrode 42 at the distal end portion 22 and a ring electrode 44 proximate to the distal end portion 22. The tip electrode 42 is electrically connected to the first electrical terminal 30. The ring electrode 44 is connected to the second electrical terminal 32. In an alternative embodiment, the header assembly 40 may include only the tip electrode 42 without a corresponding ring electrode. The header assembly 40 may also includes a heat spreader 38 provided thereon to convey thermal energy away from the header assembly 40. Optionally, the heat spreader 38 may be removed.

The header assembly 40 includes a fixation mechanism 41 that functions to interlock the lead 12 within the cardiac tissue at the implantation site and thereby prevent inadvertent displacement of the distal end portion 22 once the lead 12 is implanted. In the illustrated embodiment, the fixation mechanism 41 is represented by a screw-in helix that penetrates the cardiac tissue to anchor the lead 12 thereto.

Figure 3A:
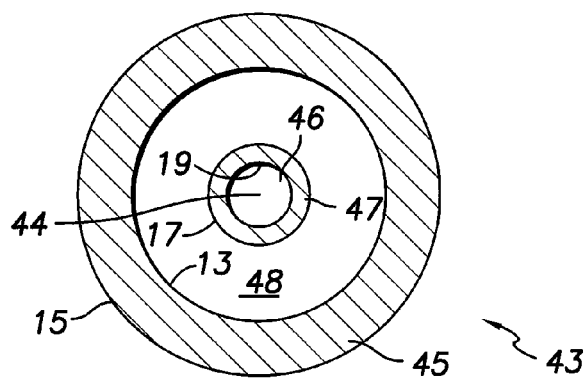
FIG. 3A illustrates a cross sectional view of a lead body for a lead that may be utilized in accordance with one embodiment.

FIG. 3A illustrates a cross sectional view of a lead body 43 for a lead that may be utilized in accordance with one embodiment. The lead body 43 is symmetric and may represent a pacing lead that includes an outer sheath or tubular layer 45 separated from an inner sheath or tubular layer 47. The inner layer 47 surrounds a central lumen 46, while the space between the inner and outer layer 47 and 45 represents an outer lumen 48. The inner layer has inner and outer diameter surfaces 19 and 17, respectively. The outer layer 45 has inner and outer diameter surfaces 13 and 15, respectively. The inner and outer lumen 46 and 48 are arranged concentric with one another and are centered about a longitudinal axis 44 of the lead body 43. The inner and outer lumen 46 and 48 are symmetrically arranged about the longitudinal axis 44.

Figure 3B:
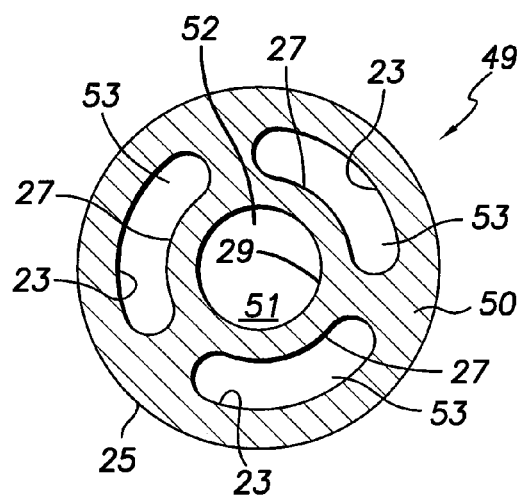
FIG. 3B illustrates a cross-sectional view of a lead body for a lead that may be utilized in accordance with one embodiment.

FIG. 3B illustrates a cross sectional view of a lead body 49 for a lead that may be utilized in accordance with one embodiment. The lead body 49 is symmetric and may represent a pacing lead, an ICD lead and the like that includes a body core 50 with a central lumen 51 provided therein and centered at a longitudinal axis 52 of the lead body 49. The body core 50 also includes multiple peripheral lumen 53 that are radially spaced from the longitudinal axis 52. The body core 50 has an inner and outer diameter surfaces 29 and 27 for the lumen 51 and inner and outer diameter surfaces 23 and 25. The surfaces 27 and 23 need not extend entirely about the axis 52, but instead are separated by the body core 50. The peripheral lumen 53 are circumferentially spaced from one another and symmetrically arranged about a perimeter of the body core 50. The peripheral lumen 53 each have a generally oval shape that is arcuate about the longitudinal axis 52.

Figure 3C:
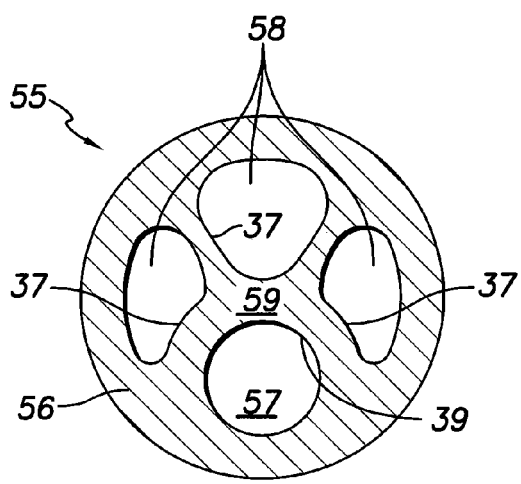
FIG. 3C illustrates a cross-sectional view of an asymmetric lead body that may be utilized in accordance with another embodiment.

FIG. 3C illustrates a cross sectional view of an asymmetric lead body 55 that may be utilized in accordance with another embodiment. The lead body 55 may represent a pacing lead, an ICD lead and the like that includes a body core 56 with a primary lumen 57 provided therein and offset from a longitudinal axis 59 of the lead body 55. The body core 56 also includes multiple secondary lumen 58 that are radially spaced from the longitudinal axis 59. The secondary lumen 58 are spaced proximate one another and grouped asymmetrically in a peripheral area of the body core 56. The secondary lumens 58 each have a generally trapezoidal shape. The body core 56 has an inner diameter surface 39 that surrounds lumen 39 and multiple inner diameter surfaces 37 that surround lumen 58. The inner and outer layers 47 and 45 and body cores 47, 50, 56 are made of a base material which is an insulating, flexible, dielectric material such as polytetrafluoroethylene (PTFE), ethylene tetrafluoroethylene (ETFE) or a silicone based polymer.

One or more of the lumen 46, 48, 51, 53, 57, 58 receive a multi-layer coil in accordance with various embodiments as described herein. Optionally, the number and configuration of lumen may vary depending upon the type of lead. The multiplayer coils may be used in a variety of lead types with a variety of lumen positions and shapes. Also, the lumen 46, 48, 51, 53, 57, 58 and other types of lumen may receive winding turn connective layers on the inner diameter surfaces and/or outer diameter surfaces as in FIGS. 10-15.

Figure 4:
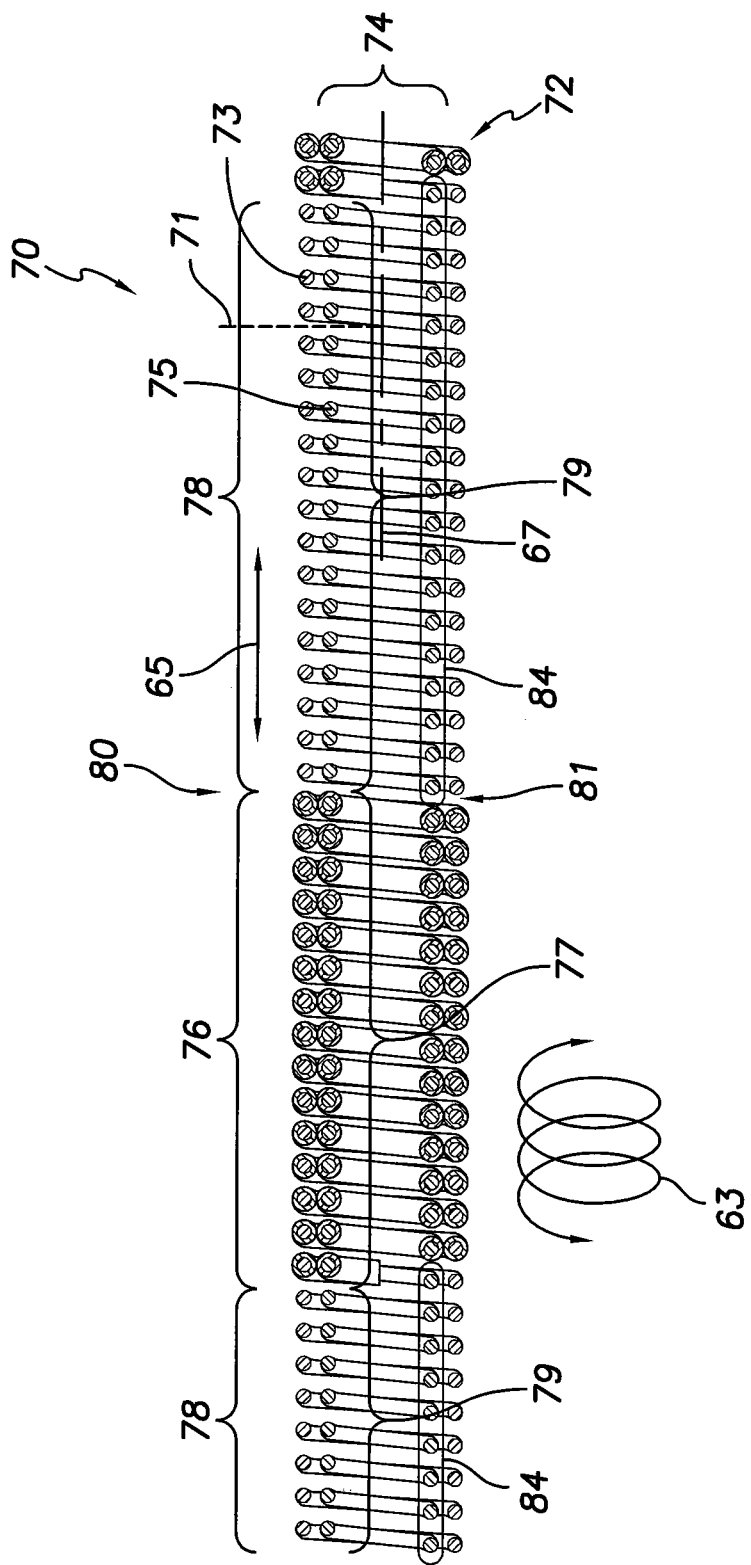
FIG. 4 illustrates a multi-layer coil formed in accordance with an embodiment.

FIG. 4 illustrates a multi-layer coil 70 formed in accordance with an embodiment of the present invention. The multi-layer coil 70 is located within a single common lumen in a lead body. The coil 70 extends at least partially along a length of the lead body. For example, the coil 70 may be utilized only proximate the distal end of a lead, or only proximate the distal end and intermediate portions of a lead body. Optionally, the coil 70 may extend along the entire length of the lead body. The coil 70 includes an outer winding 72 and an inner winding 74 located concentrically within the outer winding 72. Each of the windings 72 and 74 are structurally continuous, conductive wires (also referred to as filars) that electrically represent a string of one or more inductors (or RF chokes) and one or more bare coil segments.

The outer winding 72 has a pattern of insulated segments 76 and bare, non-insulated segments 78 alternately located along a length of the coil 70. The inner winding 74 has a pattern of insulated segments 77 and bare, non-insulated segments 79 alternately located along a length of the coil 70. In the example of FIG. 4, each of the windings 72 and 74 includes a single filar. Optionally, each of the windings 72 and 74 may include multiple filars that are individually coated within insulation within the insulated segments 76 and 77. In FIG. 4, the insulated segments 76 and 77 radially overlap and align with one another, and the non-insulated segments 78 and 79 radially overlap and align with one another. Optionally, the inner and outer windings 74 and 72 may be shifted to stagger the patterns such that the insulated segment 76 at least partially or entirely radially overlaps and aligns with the non-insulated segment 79, and the insulated segment 77 aligns with the next successive non-insulated segment 78.

The inner and outer windings 74 and 72 are formed of winding turns 75 and 73. The winding turns 75 are arranged adjacent one another and oriented at an acute pitch (denoted at 71) with respect to a longitudinal axis 67 of the coil 70. The winding turns 73 are also oriented at an acute pitch relative to the axis 67, which may be the same or different from pitch 71. The coil 70 has alternating insulated and non-insulated sections 76, 77 and 78, 79, respectively. Because the wire is a mechanically continuous wire, transition points 80, 81 between the insulated and non-insulated sections 76,77 and 78,79 are mechanically continuous and do not require any means of joining such as soldering, welding, etc. The non-insulated segments 79 of the inner winding 74 form a winding turn connective layer (a portion of which is denoted at 84) that interconnects the winding turns 73 within the non-insulated segments 78 of the outer winding 72 to one another as a single circuit in the longitudinal direction 65 along the length of the coil 70.

By connecting adjacent winding turns 73 and 75 to one another, a current flow path is maintained along the longitudinal direction 65, thereby preventing a spiral current flow path radially about the axis 74 (as denoted by spiral path 63). A longitudinal current flow path is maintained even when the lead is bent and deformed during use. The longitudinal current flow path also exhibits substantially stable and constant DC resistance in the non-insulated segments 78 and 79 even when bent or other wise deformed during normal use.

Figure 5:
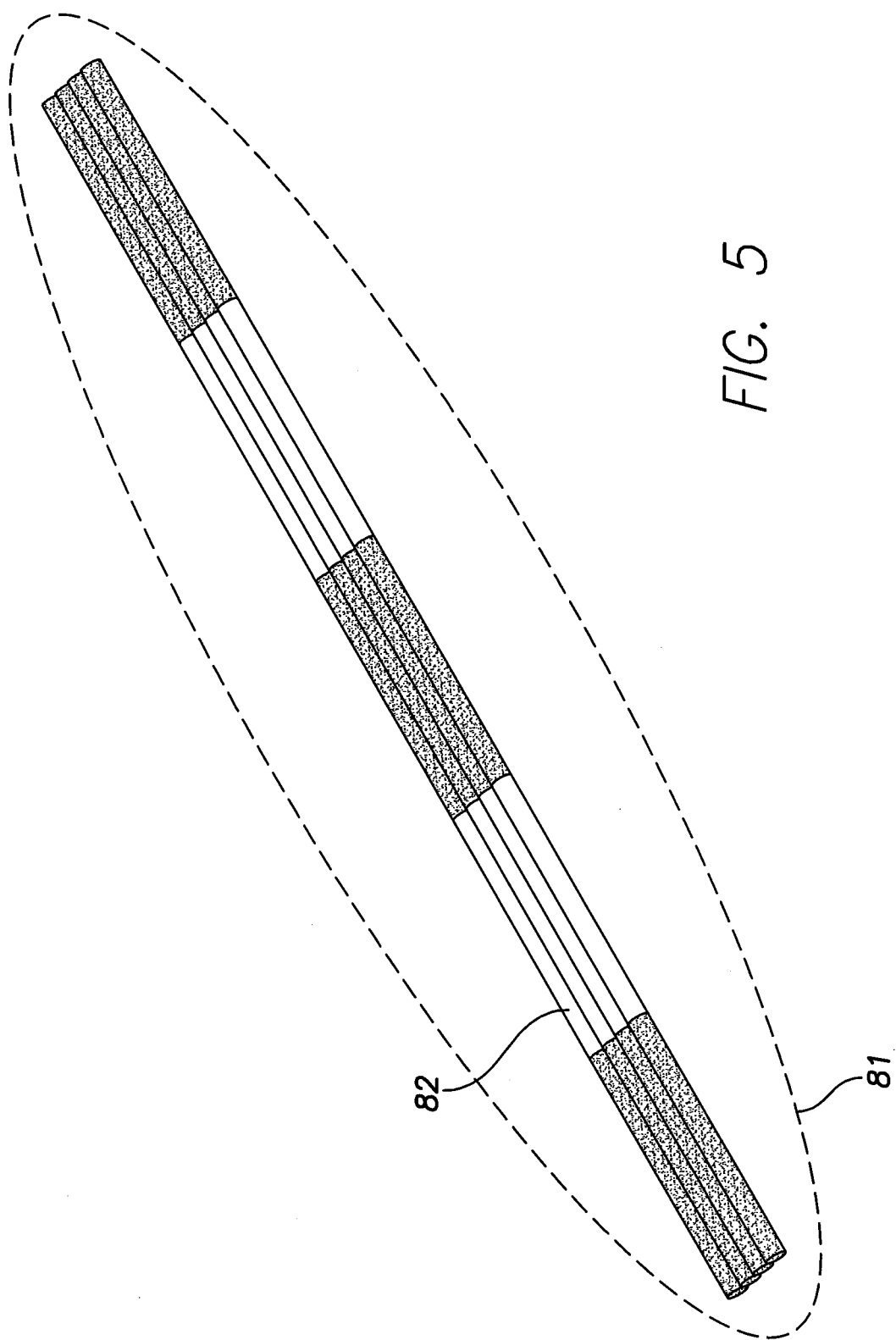
FIG. 5 illustrates a portion of a bundle of filars before being wound into a spiral shape to form a winding in accordance with an embodiment.

FIG. 5 illustrates a portion of a bundle 81 of filars 82 before being wound into a spiral shape to form a winding. In FIG. 5, the bundle 81 of individual filars 82 is located adjacent and secured to one another before being wrapped around a tubular structure to form a winding. It will be understood by those of skill in the art that instead of the single filar as in FIG. 4, multiple continuous filars as shown in FIG. 5, could be used. Additionally, the windings 72 and 74 could comprise more insulated and bare segments than shown, and the size, spacing, and insulated/non-insulated pattern of the segments can be varied within the spirit and scope of the present invention.

The coil 70 may be formed by wrapping a single filar (or multiple filars in a bundle) around a support structure to form the inner winding 74 and then wrapping a single filar (or multiple filars in a bundle) around the inner winding 74 to form the outer winding 72. Alternatively, the inner and outer windings 74 and 72 may be formed separately and then loaded axially over one another. In certain embodiments, the alternating insulated and non-insulated segments 76, 77 and 78, 79, of the multi-layer coil 70 may be created by a removal process that removes partial insulation sections from a fully insulated wire by chemical, mechanical, optical, or thermal means (e.g., chemical etching, mechanical grinding, laser burning, etc.). In other embodiments, the alternating insulated and non-insulated segments 76, 77 and 78, 79, of the multi-layer coil 70 may be created by a covering process that covers sections of a fully non-insulated (bare) wire with insulation material by means of partial extrusion, chemical deposition, etc. In some embodiments, the alternating insulated and non-insulated segments 76, 77 and 78, 79, of the multi-layer coil 70 may be formed by initially creating the inner winding 74 using fully insulated wire and subsequently removing partial insulation segments from the fully insulated wire by chemical, mechanical, optical, or thermal means. Once the inner winding 74 is completed, then the outer winding 72 may be created using fully insulated wire and subsequently removing partial segments from the fully insulated wire by chemical, mechanical, optical, or thermal means. In other embodiments, the multi-layer coil 70 may be formed by initially creating the inner winding 74 with bare wire and subsequently covering segments 77 with insulation material by means of "dipping" or chemical deposition. Thereafter, the outer winding 72 may be created with bare wire and subsequently covering segments 76 with insulation material by means of "dipping" or chemical deposition. In still other embodiments, the alternating insulated and non-insulated segments 76, 77 and 78, 79 may be created by "joining" fully insulated and non-insulated sections by means of soldering, welding, fusing, clueing, etc.

Figure 6:
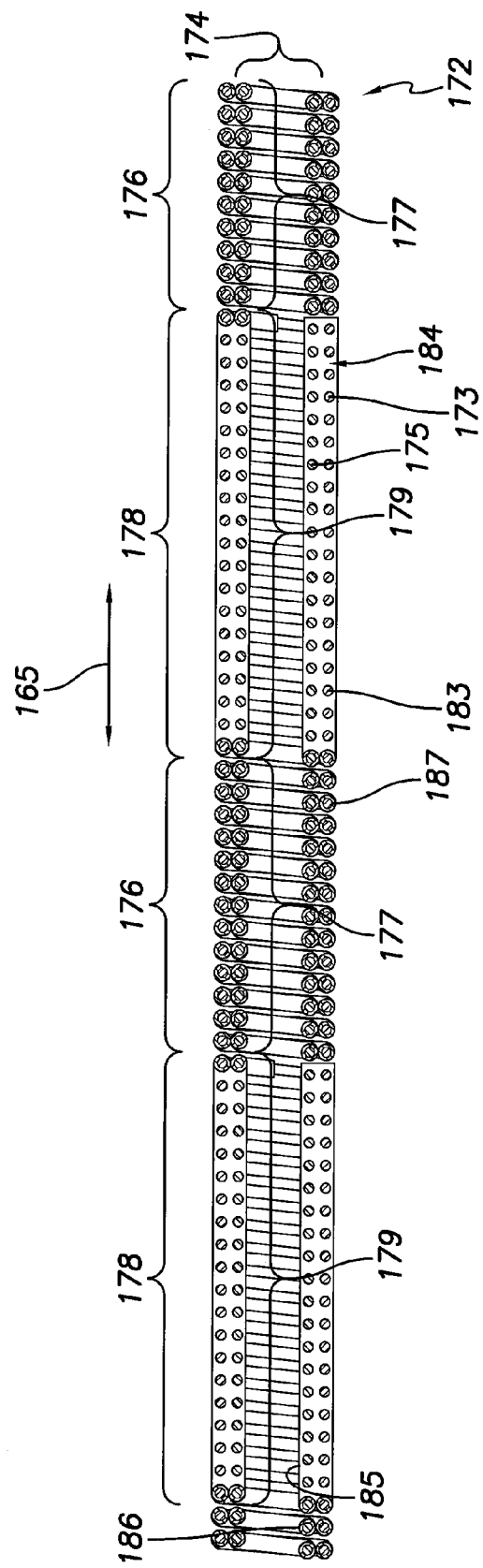
FIG. 6 illustrates a multi-layer coil formed in accordance with an embodiment of the present invention.

FIG. 6 illustrates a multi-layer coil 170 formed in accordance with an embodiment of the present invention. The coil 170 includes including an outer winding 172 and an inner winding 174 that are both formed of winding turns 173 and 175, respectively. The inner winding 174 is located concentrically within the outer winding 172. The outer winding 172 has an alternating pattern of insulated segments 176 and bare, non-insulated segments 178 located along a length of the coil 170. The inner winding 174 also has an alternating pattern of insulated segments 177 and bare, non-insulated segments 179 located along a length of the coil 170. The bare segments 178, 179 include a winding turn connective layer 184 provided within the gaps between and surrounding, the winding turns 173 and 175 of the windings 172, 174. The connective layer 184 may entirely enclose the filar/filars within one or both of the bare segments 178, 179 and form an outer surface 183 that is substantially aligned with, and has a common outer diameter as, outer surface 187 of the outer winding 172. The connective layer 184 may have an inner surface 185 that is substantially aligned with, and has a common inner diameter as, the inner surface 186 of the inner winding 174. The winding turn connective layer 184 bonds adjacent winding turns 173 and 175 to one another to form and maintain a current flow path along a longitudinal direction 165 even when bent.

Optionally, the connective layer 184 may represent a conductive polymer coating, film, shrink tubing, or ring that may be added to the bare non-insulated segments 178 and 179 such that the winding turns 173 and 175 are bonded together and electrically connected as one body or circuit. For example, silicone rubber filled with the micro or nano particles of Platinum, gold, silver, carbon, etc. with a desired percentage (for example, 90%) may be used as a conductive polymer coating. Alternatively, commercially available conductive polymer materials may be used. The conductive polymer may be used for either single filar or multifilar coils.

Any stiffness increase introduced by the soft conductive polymer coating or film is minor. For example, 0.0005"~0.005" diameter wire of MP35N, DFT, etc. plus 0.0001"~0.003" thick insulation coating of ETFE, PTFE, Polyimide, etc. may be used as the insulated wires for the zebra coil or cable. By directly adding a conductive polymer coating or film, the coil 170 may be used in lead bodies with regular inner and outer insulation tubing.

Figure 7:
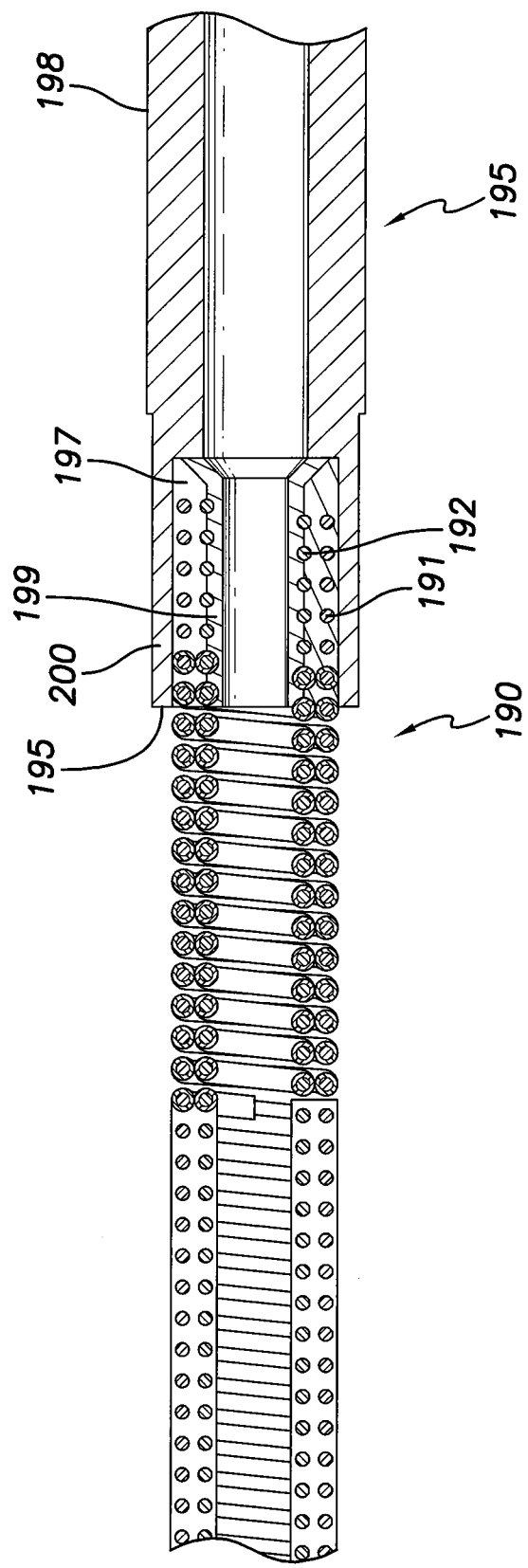
FIG. 7 illustrates a side sectional view of a termination connection between the multi-layer coil and a pin at the proximal end portion of a lead in accordance with an embodiment.

FIG. 7 illustrates a side sectional view of a termination connection between the multi-layer coil 170 and a pin 195 at the proximal end portion 190 of a lead in accordance with an embodiment of the present invention. The pin 195 is configured to be connected, at end 198, to a header of an implantable medical device. The pin 195 includes a lead engaging end 196 that has an interior cavity 197. The cavity 197 opens onto the lead engaging end 196. The proximal end portion 190 of the coil 170 includes bare end segments 191 and 192 on the outer and inner windings 172 and 174, respectively, that do not include insulation, nor the connective layer 184. The bare end segments 191 and 192 are both loaded in common through the lead engaging end 196 into the cavity 197 in the pin 195. The cavity 197 is formed between inner and outer pin walls 199 and 200. The inner and outer pin walls 199 and 200 may be crimped together to secure the bare end segments 191 and 192 to the pin 195. Optionally, the bare end segments 191 and 192 may be secured to the pin 195 through solder or other securing means.

Figure 8:
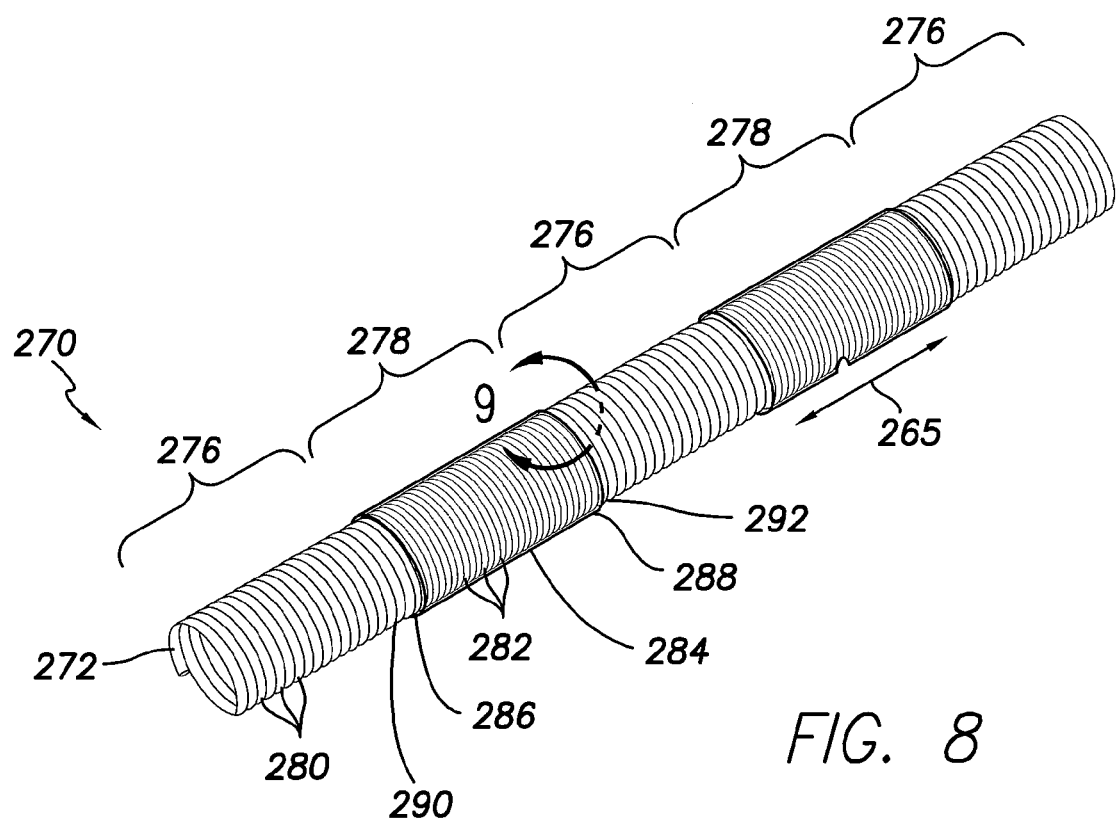
FIG. 8 illustrates a side perspective view of a multi-layer coil formed in accordance with an embodiment.

FIG. 8 illustrates a side perspective view of a multi-layer coil 270 formed in accordance with an embodiment. The coil 270 may be utilized in a wide variety of leads for a wide variety of purposes. For example, the coil 270 may be an inner or outer coil in a bradycardia lead, a tachycardial lead, an EP catheter, a CRT lead and the like. The coil 270 is located within a single common lumen in a lead body, such as in any one lumen illustrated in FIGS. 3A-3C. The coil 270 extends at least partially along a length of the lead body. The coil 270 includes a winding 272 formed from structurally continuous, conductive wires that electrically represent a string of one or more inductors (or RF chokes) and one or more bare coil segments. The winding 272 has an alternating pattern of insulated segments 276 and bare, non-insulated segments 278 located along a length thereof. In the example of FIG. 8, the winding 272 includes a single filar, but multiple filars may be used. The filar is coated with insulation within the insulated segments 276.

The insulated segments 276 are formed from multiple winding turns 280 that are arranged adjacent to one another. The non-insulated segments 278 are also formed from multiple winding turns 282 that are arranged adjacent to one another. The winding turns 282 of the non-insulated segments 278 are covered with a winding turn connective layer 284. The connective layer 284 is added at least to the outer diameter surface of the winding turns 282 in the non-insulated segments 278. Each insulated segment 276 includes an initial winding turn 290 and a final winding turn 292 immediately prior to the next successive non-insulated segment 278. Each of the connective layers 284 spans the entire corresponding non-insulated segment 278 and has edges 286 and 288 that terminate at the initial and final winding turns 290 and 292 of the preceding and succeeding insulated segments 276. The connective layer 284 may constitute a conductive coating, a film, a shrink tubing, a ring or the like, that forms a current flow path in a longitudinal direction 265.

Figure 9:
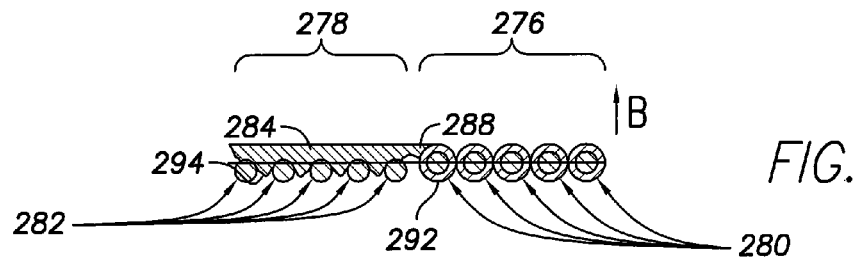
FIG. 9 illustrates a representative cross-sectional view of area A in FIG. 8 to better show a portion of the coil.

FIG. 9 illustrates a representative cross-sectional view of area A in FIG. 8 to better show a portion of the coil 270. FIG. 9 shows a series of the insulated winding turns 280 from a portion of one insulated segment 276 which precede a series of non-insulated winding turns 282 from a portion of one non-insulated segment 278. A portion of the connective layer 284 is also illustrated in cross-section. The connective layer 284 has edge 288 that extends to and terminates at the final winding turn 292 of the insulated segment 276. In the example of FIG. 9, the connective layer 284 is formed as a conductive polymer coating or film that flows into and fills gaps 294 that would otherwise exist between the winding turns 282. By way of example, the thickness of the connective layer 284 in the radial outward direction B may be the same as, or similar to, the thickness of the insulation coating on the winding turns 280 in the insulated segments 276.

The connective layer 284 adds another electrical circuit to connect the winding turns 282 in the bare segments 278. This additional circuit connection maintains stable and small DC resistance during the cyclical lead deforming in clinical conditions. Various embodiments for additional circuits are described herein for bare segments, as well as for application to inner and outer insulation tubing within a lead.

Figure 10:
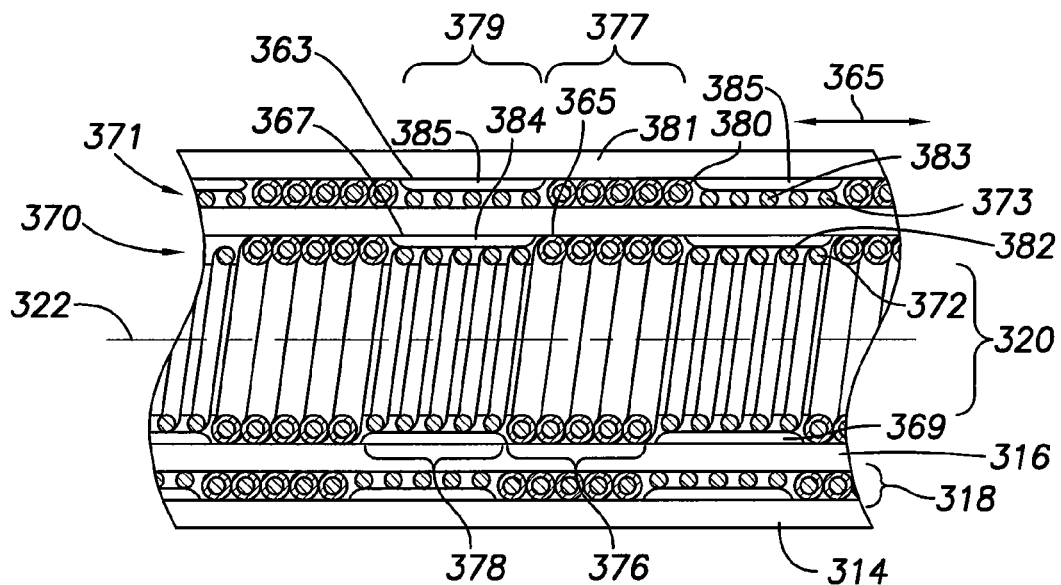
FIG. 10 illustrates a cross-sectional view of a portion of a lead body that utilizes a multi-layer coil formed in accordance with an alternative embodiment.

FIG. 10 illustrates a cross sectional view of a portion of a lead body 312 that utilizes a multi-layer coil 370 formed in accordance with an alternative embodiment. The lead body 312 includes a coaxial core structure in which an insulated outer sheath or tubular layer 314 extends along an entire length of the lead body 312. An insulated inner tubular layer 316 is located concentrically within the outer tubular layer 314. The inner and outer tubular layers 316 and 314 are spaced apart from one another to form an outer lumen 318 therebetween. The inner tubular layer 316 has a hollow core to form an inner lumen 320. The inner and outer lumen 320, 316 and the inner and outer tubular layers 316, 314 are all arranged concentrically about longitudinal axis 322.

The inner lumen 320 receives a first multi-layer inner coil 370, while the outer lumen 318 receives an multi-layer outer coil 371. The inner coil 370 includes a winding 372 that has a pattern of insulated segments 376 and bare, non-insulated segments 378 located along a length thereof. A filar is coated with insulation within the insulated segments 376. The insulated segments 376 in the winding 372 are formed from multiple winding turns 380 that are arranged adjacent to one another, while the non-insulated segments 378 are also formed from multiple winding turns 382 that are arranged adjacent to one another. The winding turns 382 of the non-insulated segments 378 are covered with a winding turn connective layer 384. The connective layer 384 is added to the outer diameter surface 369 of the winding turns 382 in the non-insulated segments 378. Each connective layer 384 spans the entire corresponding non-insulated segment 378 and has radial edges 367 and 365 that terminate at the initial and final coil turns of the preceding and succeeding insulated segments 376. The radial edges 367 and 365 extend about a longitudinal axis 0fo the winding 372. The edges 367 and 365 are located proximate transition points between winding turns 382 and winding turns 380.

The outer coil 371 includes a winding 373 that is structurally continuous, conductive wires. The winding 373 has a pattern of insulated segments 377 and bare, non-insulated segments 379 located along a length thereof. The insulated segments 377 in the winding 373 are formed from multiple winding turns 381 that are arranged adjacent to one another, while the non-insulated segments 379 are also formed from multiple winding turns 383 that are arranged adjacent to one another. The winding turns 383 of the non-insulated segments 379 are covered with a winding turn connective layer 385 that is added to the outer diameter surface 363 of the winding turns 383 in the non-insulated segments 379. The connective layers 384 and 385 form current flow paths along a longitudinal direction 365 of the coils 370 and 371.

Figure 11:
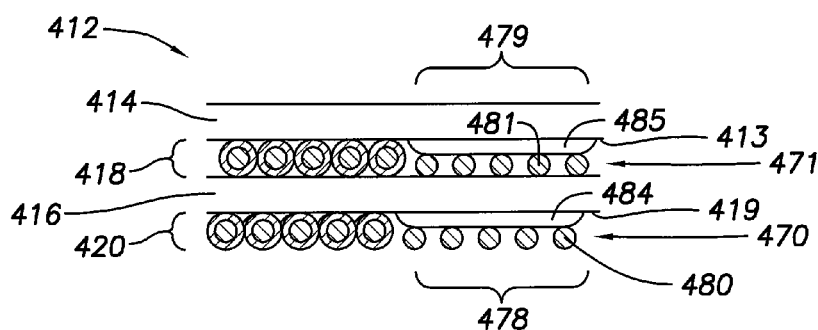
FIG. 11 illustrates a cross-sectional side view of a portion of a lead body that utilizes multi-layer coils formed in accordance with an alternative embodiment.

FIG. 11 illustrates a cross-sectional side view of a portion of a lead body 412 that utilizes multi-layer coils 470 and 471 formed in accordance with an alternative embodiment. The lead body 412 includes a body core that includes at least two lumen, such as a structure in which an insulated outer tubular layer 414 extends along an entire length of the lead body 412. An insulated inner tubular layer 416 is located concentrically within the outer layer 414 (similar to the configuration of FIG. 3A). The inner and outer tubular layers 416 and 414 are spaced apart from one another to form an outer lumen 418 therebetween. The inner tubular layer 416 has a hollow core to form an inner lumen 420. The inner and outer lumen 420, 418 and the inner and outer tubular layers 416, 414 are all arranged concentrically about a longitudinal axis of the lead body 412.

The inner and outer layers 416 and 418 each have a winding turn connective layer 484 and 485, respectively. The connective layers 484 and 485 are located to align with the winding turns 480 and 481 of the non-insulated segments 478 and 479, respectively. The connective layers 484 and 485 are located on the inner diameter surfaces 419 and 413 of the inner and outer layers 416 and 418, respectively. The connective layer 484 engages and electrically bonds adjacent winding turns 480 as a single circuit. The connective layer 485 engages and electrically bonds adjacent winding turns 481 as a single circuit.

Figure 12:
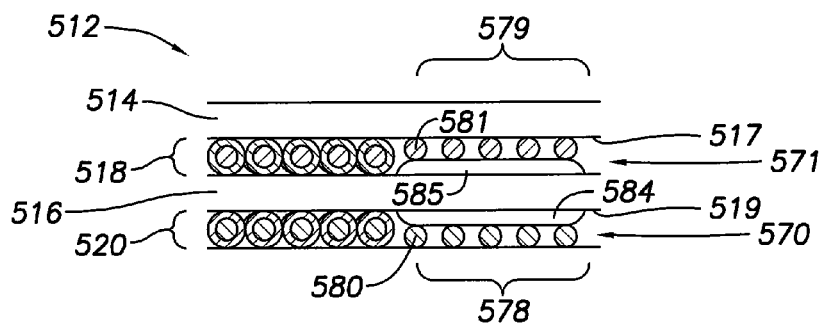
FIG. 12 illustrates a cross-sectional side view of a portion of a lead body that utilizes multi-layer coils formed in accordance with an alternative embodiment.

FIG. 12 illustrates a cross-sectional side view of a portion of a lead body 512 that utilizes multi-layer coils 570 and 571 formed in accordance with an alternative embodiment. The lead body 512 includes a coaxial core structure (similar to FIG. 3A) in which an insulated outer tubular layer 514 extends along an entire length of the lead body 512. An insulated inner tubular layer 516 is located concentrically within the outer layer 514. The inner and outer tubular layers 516 and 514 are spaced apart from one another to form an outer lumen 518 therebetween. The inner tubular layer 516 has a hollow core to form an inner lumen 520. The inner and outer lumen 520, 518 and the inner and outer tubular layers 516, 514 are all arranged concentrically about a longitudinal axis of the lead body 512.

In the embodiment of FIG. 12, the inner layer 516 has an inner surface 519 and an outer diameter surface 517, each of which has a winding turn connective layer 584 and 585, respectively, provided thereon. The connective layers 584 and 585 are located to align with the winding turns of the non-insulated segments 578 and 579, respectively. The connective layers 584 and 585 are located on the inner and outer diameter surfaces 519 and 517 during manufacture of the inner tubular layer 516. The connective layer 584 engages and electrically bonds adjacent winding turns 580 on the multi-layer coil 570 to form a single circuit. The connective layer 585 engages and electrically bonds adjacent winding turns 581 on the multi-layer coil 571 to form a single circuit.

Figure 13:
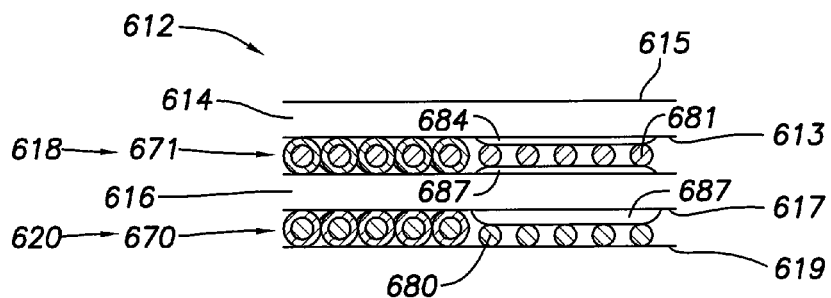
FIG. 13 illustrates a cross-sectional side view of a portion of a lead body that utilizes multi-layer coils formed in accordance with an alternative embodiment.

FIG. 13 illustrates a cross-sectional side view of a portion of a lead body 612 that utilizes multi-layer coils 670 and 671 formed in accordance with an alternative embodiment. The lead body 612 includes a coaxial core structure with an insulated inner tubular layer 616 located concentrically within an insulated outer layer 614. The inner and outer tubular layers 616 and 614 are spaced apart from one another to form an outer lumen 618 therebetween. The inner tubular layer 616 has a hollow core to form an inner lumen 620. The inner and outer lumen 620, 618 and the inner and outer tubular layers 616, 614 are all arranged concentrically about a longitudinal axis of the lead body 612.

In the embodiment of FIG. 13, the inner layer 616 has an inner diameter surface 619 and an diameter outer surface 617, each of which has a winding turn connective layer 687 and 685, respectively, provided thereon. The outer layer 614 has an inner diameter surface 613 and an outer sheath surface 615. A connective layer 684 is provided on the inner diameter surface 613. The connective layers 684, 685 and 687 are located to align with the winding turns 680 and 681 of the inner and outer multi-layer coils 670 and 671. The connective layers 684, 685 and 687 are inserted during manufacture of the inner and outer layers 614 and 616. The connective layers 684 and 685 engage and electrically connect to adjacent winding turns 681 on the multi-layer coil 671 to form a single circuit. The connective layer 687 engages and electrically connects adjacent winding turns 680 on the multi-layer coil 670.

Figure 14:
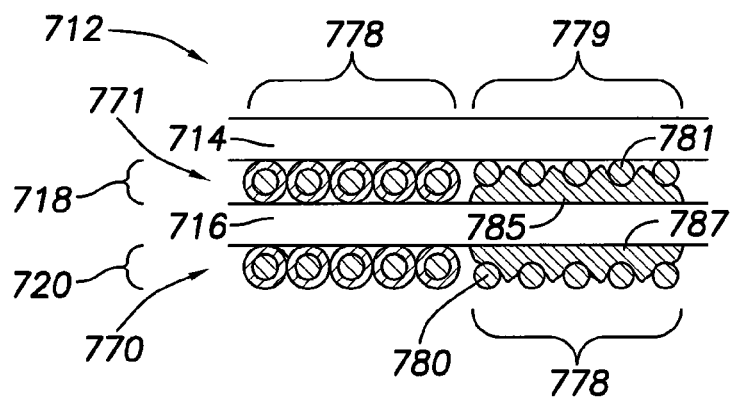
FIG. 14 illustrates a cross-sectional side view of a portion of a lead body that utilizes multi-layer coils formed in accordance with an alternative embodiment.

FIG. 14 illustrates a cross-sectional side view of a portion of a lead body 712 that utilizes multi-layer coils 770 and 771 formed in accordance with an alternative embodiment. The lead body 712 includes a coaxial core structure in which an insulated outer tubular layer 714 extends along an entire length of the lead body 712. An insulated inner tubular layer 716 is located concentrically within an insulated outer tubular layer 714. The inner and outer tubular layers 716 and 714 are spaced apart from one another to form an outer lumen 718 therebetween. The inner tubular layer 716 has a hollow core to form an inner lumen 720. The winding turns 781 of the non-insulated segment 779 of the outer coil 771 have an inner diameter surface that has a winding turn connective layer 785 provided thereon. The winding turns 780 of the non-insulated segments 778 of the inner coil 770 have an outer diameter surface that has a winding turn connective layer 787 provided thereon. The connective layers 785 and 787 engage and electrically connect to corresponding adjacent winding turns 781 and 780, respectively.

Optionally, alternative combinations of winding turn connective layers may be utilized. For example, winding turn connective layers may be provided on the outer diameter surface of one or more of the non-insulated segments in one or more multi-layer coils. In the same lead body, winding turn connective layers may be provided on the outer diameter surface of the insulated inner tubular layer and aligned with the non-insulated segments in the multi-layer coil located radially about the inner tubular layer.

Optionally, the coil configurations of FIGS. 11-14 may be utilized with leads having body cores that do not include concentric inner and outer layers. Instead, the coil configurations of FIGS. 11-14 may be utilized with the body cores of FIGS. 3B and 3C or other body core structures that have one or more lumen. The connective layer (e.g., 584, 585, 684, 685, 687, etc.) may be applied to the inner surface of any lumen regardless of the lumen cross-sectional shape.

Figure 15:
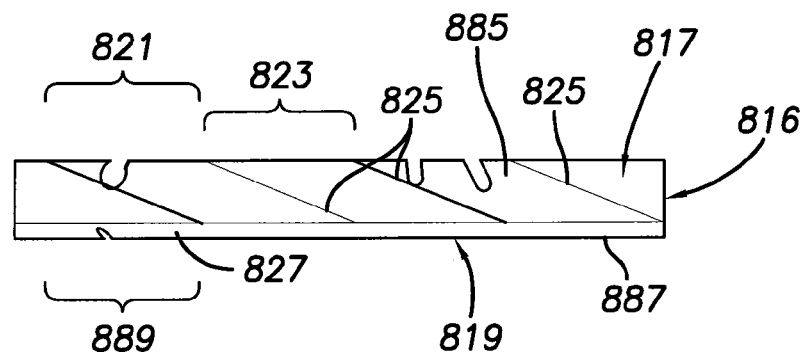
FIG. 15 illustrates a portion of an insulated sheath flattened, such as before being shaped into a tubular layer, that may be used in accordance with an alternative embodiment.

FIG. 15 illustrates a portion of an insulated sheath 816 flattened, such as before being shaped into a tubular layer, that may be used in accordance with an alternative embodiment. For example, the insulated sheath 816 may be rolled to form one of the inner tubular layers 47, 316, 416, 516, 616 discussed herein. The insulated sheath 816 includes an outer surface 817 and an inner surface 819 that face corresponding lumens (e.g., 718 and 720). The outer surface 817 has a series of conductive strips 885 formed thereon and arranged in a striped pattern. Conductive sections 821 of the conductive strips 885 are separated by insulated sections 823. The conductive strips 885 have transverse edges 825 that are arranged to traverse a width of the sheath 816 at an acute angle relative to a longitudinal side 827 of the sheath 816.

Optionally, conductive strips 887 may be provided on the inner surface 819 as well. The conductive strips 887 are separated from one another by insulated sections 889 and are arranged at an acute angle to the side 827 of the layer 816. The conductive strips 885 and 887 may constitute a conductive coating, a film, a shrink tubing, a ring or the like that may be added on the inner diameter surface and/or outer diameter surface of the inner insulation winding 174. The layer 816 may be formed of Silicone, Polyurethane, Optim, GORE, etc. that is coated with a specific pattern using the conductive polymer mentioned above, such that the conductive strips 885 and 887 are formed on one or both the inner diameter and outer diameter surfaces of the inner insulation tubular layer when the sheath 816 is wrapped using a conventional tubing thermal forming process. The pattern of the conductive strips 885 and 887 may be designed such that it will form the discrete segments that will contact (at one point at least) with the bare coil or cable segments (e.g., 579 and 578) in a zebra coil or cable.

Figure 16:
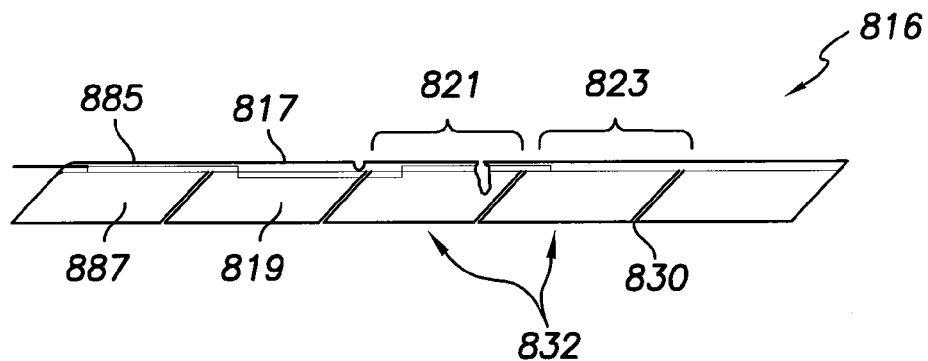
FIG. 16 illustrates the insulated sheath of FIG. 15 when wrapped into a tubular shape.

FIG. 16 illustrates the insulated sheath 816 of FIG. 15 when wrapped into a tubular shape. Once the conductive strips 885 and 887 are applied to the insulated sheath 816, the sheath 816 is wrapped into the tubular shape of FIG. 16, such as through a spiral or helical wrapping technique. Once wrapped, gaps 830 remain between adjacent spiral sections 832 of the sheath 816. A thermal forming process may be applied to close or join the gaps 830 to form a seamless insulated tubular layer.

Figure 17:
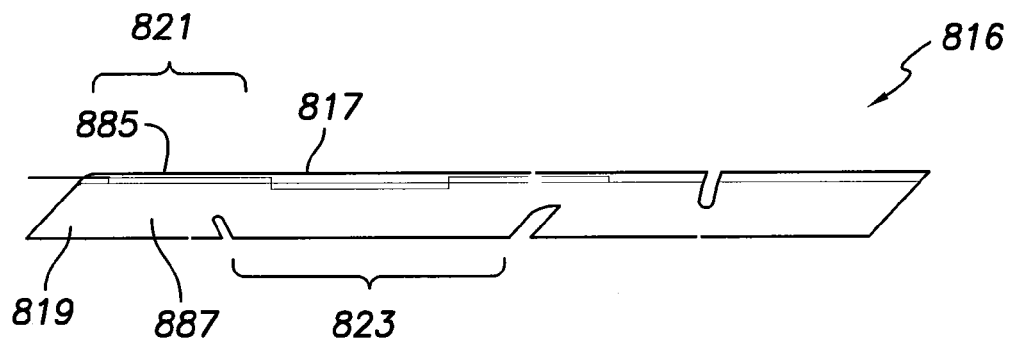
FIG. 17 illustrates the sheath of FIG. 16 after applying the thermal forming process to seal the gaps.

FIG. 17 illustrates the sheath 816 after applying the thermal forming process to seal the gaps 83. In FIG. 17, the sheath 816 is shown in cross-section to illustrate the conductive strips 887 formed on the inner surface 819 and conductive strips 885 formed on the outer surface 817. The conductive sections 821 are separated by non-insulated sections 823.

Figure 18:
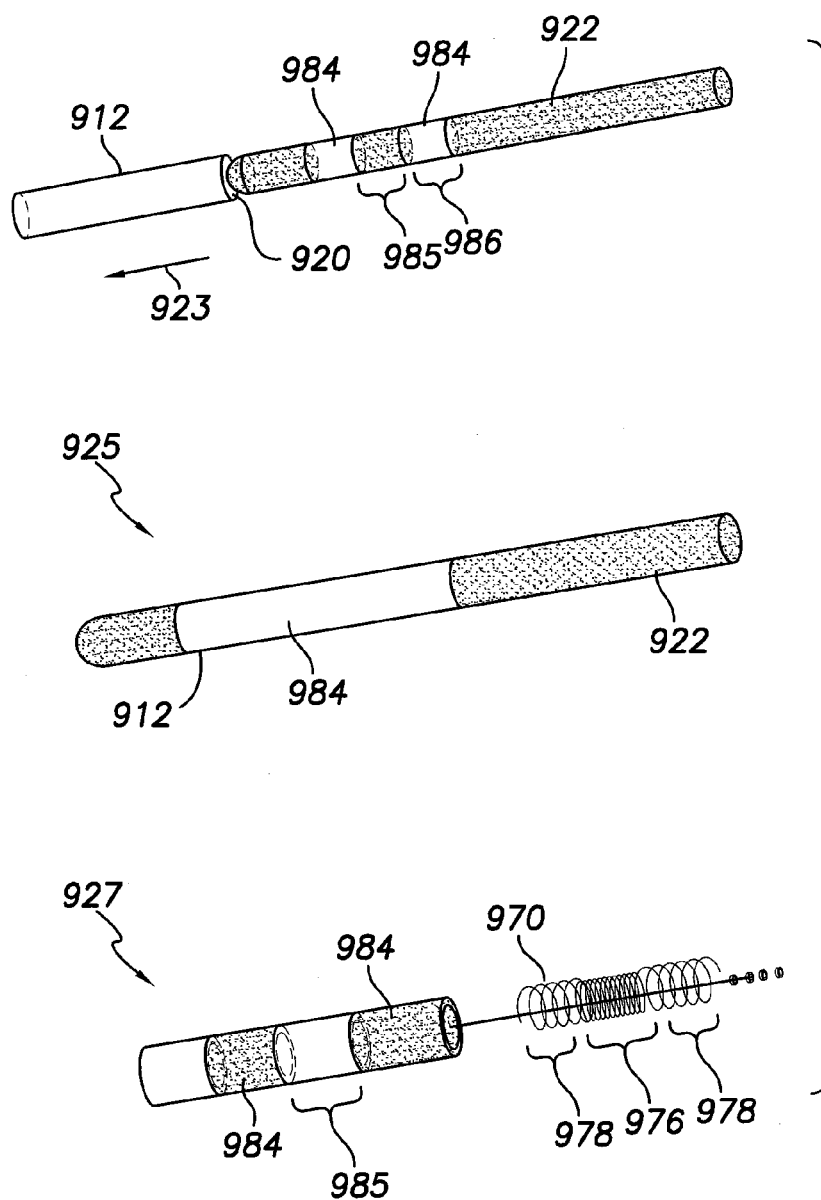
FIG. 18 illustrates an alternative process for manufacturing a lead body including a multi-layer coil.

FIG. 18 illustrates an alternative process for manufacturing a lead body including a multi-layer coil. In FIG. 18, a portion of a lead body 912 is illustrated with a open ended lumen 920. A tubular mandrel 922 is coated with rings of a conductive polymer to form winding turn connective layers 984. The connective layers 984 are spaced apart from one another by a distance 985 that corresponds to the length of an insulated segment. The lengths 986 of the connective layers 984 are determined to correspond to the length of an associated non-insulated segment. The conductive layers 984 may be formed from a variety of materials as explained throughout. The mandrel 922 is inserted in a loading direction 923 into the open end of the lumen 920 until the connective layers 984 are positioned at a desired longitudinal position within the lead body 912 (such as illustrated at loaded stage 925.)

Once the mandrel 922 is loaded into the lead body 912 to a desired position, the connective layers 984 are located proximate regions of the inner surface of the lumen 920 at which non-insulated segments of a corresponding coil will later be loaded. Next, a thermal or reforming process is applied such that the connective layers 984 become separated from the mandrel 922 and bonded to the inner surface of the lead body 912. Once the connective layers 984 are securely bonded to the lead body 912 and disengaged from the mandrel 922, the mandrel 922 is removed.

Next, at a coil loading stage 927, a coil 970 is loaded through the open end of the lumen 920. The coil 970 includes insulated segments 976 and un-insulated segments 978 alternately arranged along the length thereof. The coil 970 is loaded until the non-insulated segments 978 radially align with the connective layers 984 and the insulated segments 976 align with the insulated sections 985 located between the connective layers 984.

Optionally, the foregoing process which utilizes a mandrel to load connective layers may be applied to any lumen within a lead body. For lumen having a noncircular cross-section, the mandrel will be shaped with a similar noncircular cross-section. For example, the mandrel may be shaped to have cross-sections that resemble any of the lumen illustrated in FIGS. 3A-3C to load connective layers into any such lumen.

Optionally, embed conductive rings of conductive polymer or metal may be added in the inner diameter and/or outer diameter surfaces of the inner and/or outer insulation tubing, such that the rings will touch the bare coil or cable segments, respectively. A thermal forming process can be applied to bond the rings on the tubing inner diameter and outer diameter surfaces. A thin sheath of the above listed conductive polymer, and the conductive metal of Platinum, gold, silver, carbon, etc. can be used for the conductive rings.

Optionally, a blood seal feature, such as a rubber sealing ring, may be added to the lead distal segment, such that the blood or body fluid will be stopped from entering the lead body. This will ensure no electric short occurs between the zebra coil or cable segments by means of the conductive blood or body fluid.

The above embodiments afford additional discrete circuits over the bare non-insulated segments of a coil that are feasible for any length (not necessary the same length or uniform distributed along the lead body) of the bare segments. The above embodiments can be used for the uni-polar and multi-polar, co-axial and co-radial, single lumen and multi-lumen designs of the leads with the zebra coil or cable.

In at least certain embodiments, the multi-layer coils provide the desired electromagnetic coupling to the RF chokes between the $1^{st}$ and $2^{nd}$ layer coils, such that the lengths of the insulated coil segment or the RF chokes are much shorter than that by a single layer zebra coil, which makes it more feasible for the RF chokes to resonant at the MRI scanner working frequencies of 64 MHz and/or 128 MHz. The insulated coil segments of shorter length are less likely bent than those of longer length when the lead body is subjected to the cyclic heart beat or motion, which makes the dual layer zebra coil's RF chokes perform more stably.

The means of adding a conductive polymer to the bare coil segments will maintain stable and small DC resistance in the bare coil segments, which enhances the performances of the series of the self resonant RF chokes or low pass filters. A dual layer zebra coil configured as one body provide a desired coil stiffness to transfer the torque and push/pull forces for certain applications. In certain embodiments above, $1^{st}$ and $2^{nd}$ layer coil electromagnetic coupling achieves RF heating reduction at the inner conductor tip for the lead of the insulated inner coil plus the insulated outer coil.

Optionally, the DFT (25%~75% Ag-cored MP35N) wire of diameter 0.002"~0.005" may be used and coated or jacked with 0.0001"~0.0025" thick ETFE, PTFE, Polyimade, etc. The wire material can be of the pure MP35N, tantalum, etc. The insulated DFT wire may be ablated using soda blast, laser, etc. with desired insulated and un-insulated segment numbers and segment lengths, such that the zebra coil insulated and bare segments are obtained after the coil winding using the ablated wire. For example, the insulated and bare segment length may be 1 cm~15 cm, depending on the desired resonant frequencies of 64 MHz, 128 MHz, etc. Optionally, a dual layer coil may have only one insulated segment in the whole lead body without any bare segment for other applications.

The single filar ablated wire may be wound with a tight pitch for the 1st layer coil and continuously wound for the 2nd layer coil over the 1st layer. The zebra zones of the two layer coils may be the in the same or different locations, depending on the desired electromagnetic couplings between the 1st and 2nd layer coils. The wound direction between the two layer coils may be the same or different (e.g., right-hand or left-hand).

The bare or un-insulated segments may be filled with conductive polymer, such that the turns in the 1st and 2nd layer bare coil segments are bonded as one body or circuit in the bare segments. Silicone rubber mixed with the micro or nano particles of Platinum, Iridium, gold, silver, carbon, MP35N, etc. with a desired percentage (for example, 90% in weight) is one of the conductive polymer candidates, in addition to the commercially available conductive polymer materials.

A two layer zebra coil affords electrical redundancy for a pacing circuit. The wire diameter, coating thickness, coil diameter, and coil pitch may be designed together for a desired stiffness to transfer the required torque and take sufficient push/pull forces.

Optionally, the fully coated or jacked wire for a dual layer coil may be wound first, then the 1st and 2nd layer coil ablated together by means of the soda blast, laser, etc. striping method to make the bare segments. An ultrasonic cleaning may be used to remove the ablated residuals. A coating may be stripped by means of the soda blast, laser, etc. methods, and then joined with the helix shaft at the distal end and the pin at proximal end by means of the crimping, laser welding, etc., respectively.

At least certain embodiments of the present invention seek to maintain stable and small DC resistance in the bare coil or cable segments, in order to have desired and stable performance from of the series of insulated coil segments as self resonant RF chokes. The application of certain inventive concepts described herein may enhance the heating reduction performance of self resonant RF chokes.

It is to be understood that the invention is not limited in its application to the details of construction and the arrangement of components set forth in the description herein or illustrated in the drawings hereof. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Also, it is to be understood that phraseology and terminology used herein with reference to device or element orientation (such as, for example, terms like "central," "upper," "lower," "front," "rear," "distal," "proximal," and the like) are only used to simplify description of the present invention, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An implantable lead, comprising:
   a lead body configured to be implanted in a patient, the lead body having a distal end and a proximal end, and a lumen extending between the distal and proximal ends;
   a connector assembly provided at the proximal end of the lead body, the connector assembly configured to connect to an implantable medical device;
   an electrode provided proximate to the distal end of the lead body, the electrode configured to at least one of deliver stimulating pulses and sense electrical activity; and
   a multi-layer coil conductor located within the lumen along the lead body and electrically coupled between the connector and the electrode, the multi-layer coil including a first winding formed with multiple winding turns, the winding turns being segmented in an alternating pattern of insulated segments and non-insulated segments along at least a portion of the length of the lead body, the multi-layer coil including a winding turn connective layer extending along and electrically interconnecting the winding turns within at least one of the non-insulated segments.

2. The lead of claim 1, wherein the winding turn connective layer is located along at least one of an inner diameter surface and an outer diameter surface of the winding turns within the at least one of the non-insulated segments.

3. The lead of claim 1, wherein the winding turn connective layer constitutes one of a conductive polymer coating, a conductive film, a tubular member and a ring that bonds to the winding turns to form a single circuit.

4. The lead of claim 1, wherein the winding turn connective layer fills a void between, and electrically connects, adjacent of the winding turns to one another within the at least one of the non-insulated segments.

5. The lead of claim 1, wherein the winding turn connective layer comprises conductive strips that radially wrap about sections of the lumen, the conductive strips being spaced apart from one another along a length of the lumen and positioned to align with the non-insulated segments of the first winding.

6. The lead of claim 1, wherein the conductive strips constitute one of a conductive polymer coating, a conductive film, a tubular member and a ring that bonds to at least one of an inner diameter surface and an outer diameter surface of the lumen.

7. The lead of claim 1, wherein the winding turn conductive layer further comprises a second winding located concentrically with the first winding, at least one of the first and second windings having the pattern of insulated segments and non-insulated segments.

8. The lead of claim 7, wherein the first and second windings are co-located in a single common lumen.

9. The lead of claim 7, wherein the first and second windings are co-located in a single common lumen that is located off-axis from a longitudinal axis of the lead body.

10. The lead of claim 1, wherein the multi-layer coil comprises a single, continuous wire.

11. The lead of claim 1, wherein the insulated segments and the non-insulated segments are of substantially equal length.

12. The lead of claim 1, wherein the insulated segments and the non-insulated segments are of unequal length.

13. An implantable lead, comprising:
    a multilayer coil electrically coupled between a lead connector and a lead electrode, the multilayer coil including a first winding formed with multiple winding turns, the winding turns being segmented into an alternating pattern of insulated segments and non-insulated segments along at least a portion of the length of the lead; and a winding turn connective layer extending along and electrically interconnecting the winding turns within at least one of the non-insulated segments.

14. The coil of claim 13, wherein the winding turn connective layer includes opposed radial edges extending about a longitudinal axis of the winding, the edges being located proximate transition points between winding turns in the insulated and non-insulated segments.

15. The coil of claim 13, wherein the winding turn connective layer constitutes one of a conductive polymer coating, a conductive film, a tubular member and a ring, the winding turn connective layer bonding to the winding turns in the non-insulated segment to one another to form a single circuit having a current flow path extending along a longitudinal direction of the coil.

16. The coil of claim 13, wherein the winding turn connective layer fills voids between, and electrically connects, adjacent winding turns to one another within the at least one of the non-insulated segments.

17. The coil of claim 13, wherein the winding turn connective layer comprises a second winding located concentrically with the first winding, at least one of the first and second windings having the pattern of insulated segments and non-insulated segments.

18. The coil of claim 13, further comprising a second winding formed with multiple winding turns, the winding turns of the second winding being segmented into an alternating pattern of insulated segments and non-insulated segments along the length of the coil.

19. The coil of claim 18, wherein the second winding is aligned concentrically within the first winding, the second winding being longitudinally shifted such that the non-insulated segments of the first winding radially align with and overlap the non-insulated segments of the second winding.

20. The coil of claim 18, wherein the winding turn connective layer is provided within gaps between, and surrounds, the winding turns of each of the first and second windings in the corresponding non-insulated segments.

* * * * *